(12) United States Patent
Fedorciw et al.

(10) Patent No.: US 12,226,539 B2
(45) Date of Patent: Feb. 18, 2025

(54) ULTRAVIOLET EMITTER FOR SANITATION OF AEROSOLS

(71) Applicants: Roman Fedorciw, Avon, CT (US); Borys Krynyckyi, Manasquan, NJ (US)

(72) Inventors: Roman Fedorciw, Avon, CT (US); Borys Krynyckyi, Manasquan, NJ (US)

( * ) Notice: Subject to any disclaimer, the term of this patent is extended or adjusted under 35 U.S.C. 154(b) by 556 days.

(21) Appl. No.: 17/001,027

(22) Filed: Aug. 24, 2020

(65) Prior Publication Data
US 2021/0361807 A1   Nov. 25, 2021

Related U.S. Application Data

(60) Provisional application No. 63/040,861, filed on Jun. 18, 2020, provisional application No. 63/029,023, filed on May 22, 2020.

(51) Int. Cl.
*A61L 2/10* (2006.01)
*A61L 2/22* (2006.01)

(52) U.S. Cl.
CPC ............... *A61L 2/22* (2013.01); *A61L 2/10* (2013.01); *A61L 2202/11* (2013.01); *A61L 2202/123* (2013.01); *A61L 2202/16* (2013.01); *A61L 2202/20* (2013.01)

(58) Field of Classification Search
CPC ....................................................... A61L 2/10
See application file for complete search history.

(56) References Cited

U.S. PATENT DOCUMENTS

| | | | |
|---|---|---|---|
| 2017/0304472 A1* | 10/2017 | Neister | A61L 2/10 |
| 2020/0197550 A1* | 6/2020 | Barron | A61L 2/084 |
| 2021/0283423 A1* | 9/2021 | Anderson | A61N 5/0624 |

OTHER PUBLICATIONS

"Mighty Vue Pro 5 Diopter [2.25x] Magnifying Lamp With UV and White LEDs-ESD Safe", Jan. 27, 2020, Aven (Year: 2020).*
"Are Sterilization Lamps Worth the Investment?", Sep. 6, 2018, Diatech, https://diatechusa.com/blog/sterilization-lamps-worth-cost/ (Year: 2018).*
Mighty Vue publication date (Year: 2020).*
Sterilization Lamps publication date (Year: 2018).*

* cited by examiner

*Primary Examiner* — Kevin Joyner
(74) *Attorney, Agent, or Firm* — CANTOR COLBURN LLP

(57) ABSTRACT

A sanitation system for use in an application where contaminated aerosols are exhausted by a person includes at least one light source selectively operable to emit a light having a wavelength capable of neutralizing particles and that does not penetrate human skin. The sanitation system additionally includes a mounting system operable to mount said at least one light source. The mounting system is configured to direct the light emitted from the at least one light source toward the person such that the particles are neutralized as the particles are exhausted by the person.

12 Claims, 5 Drawing Sheets

ULTRAVIOLET EMITTER FOR SANITATION OF AEROSOLS

CROSS-REFERENCE TO RELATED APPLICATIONS

Figure 1:
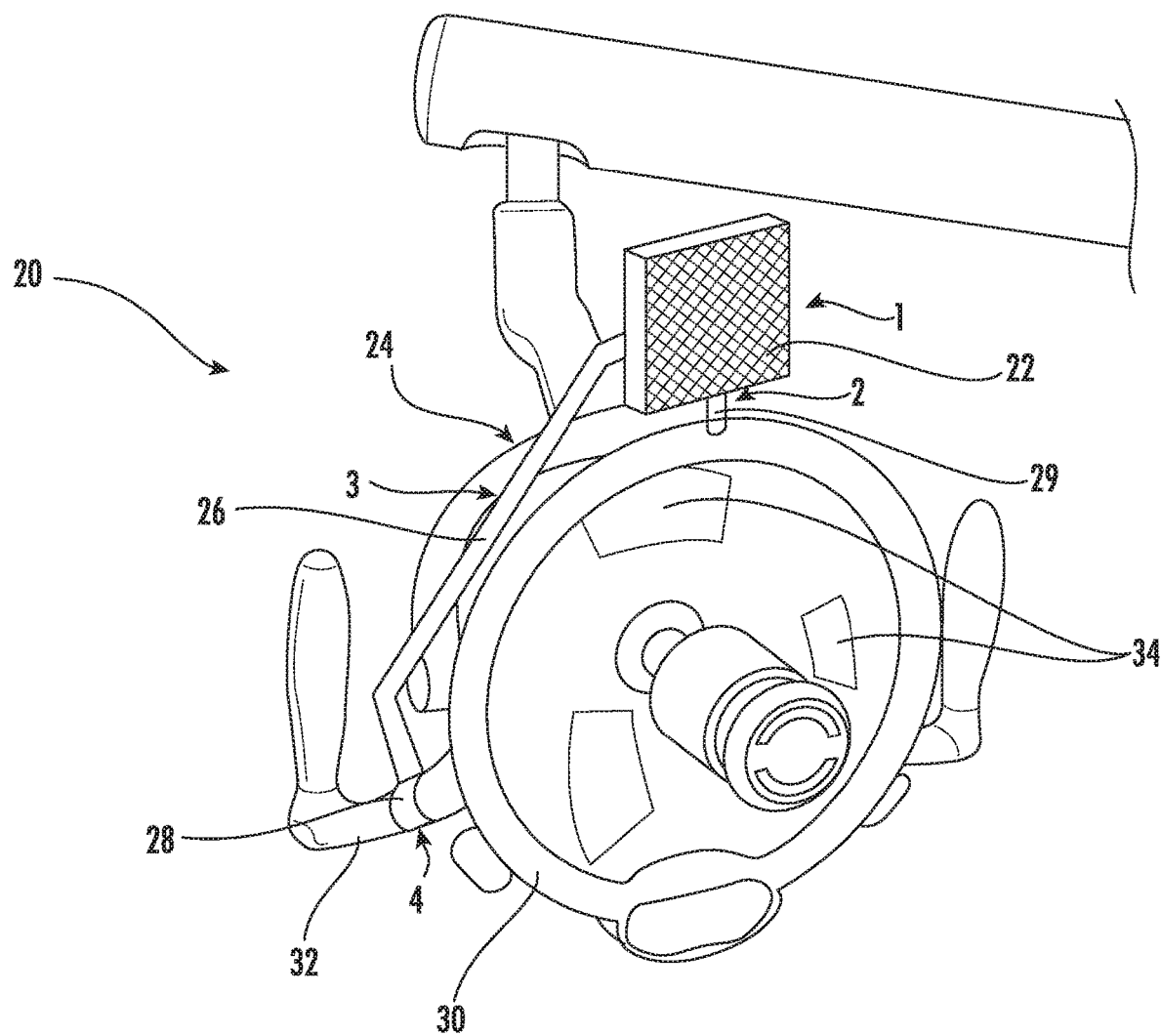
Figure 2:
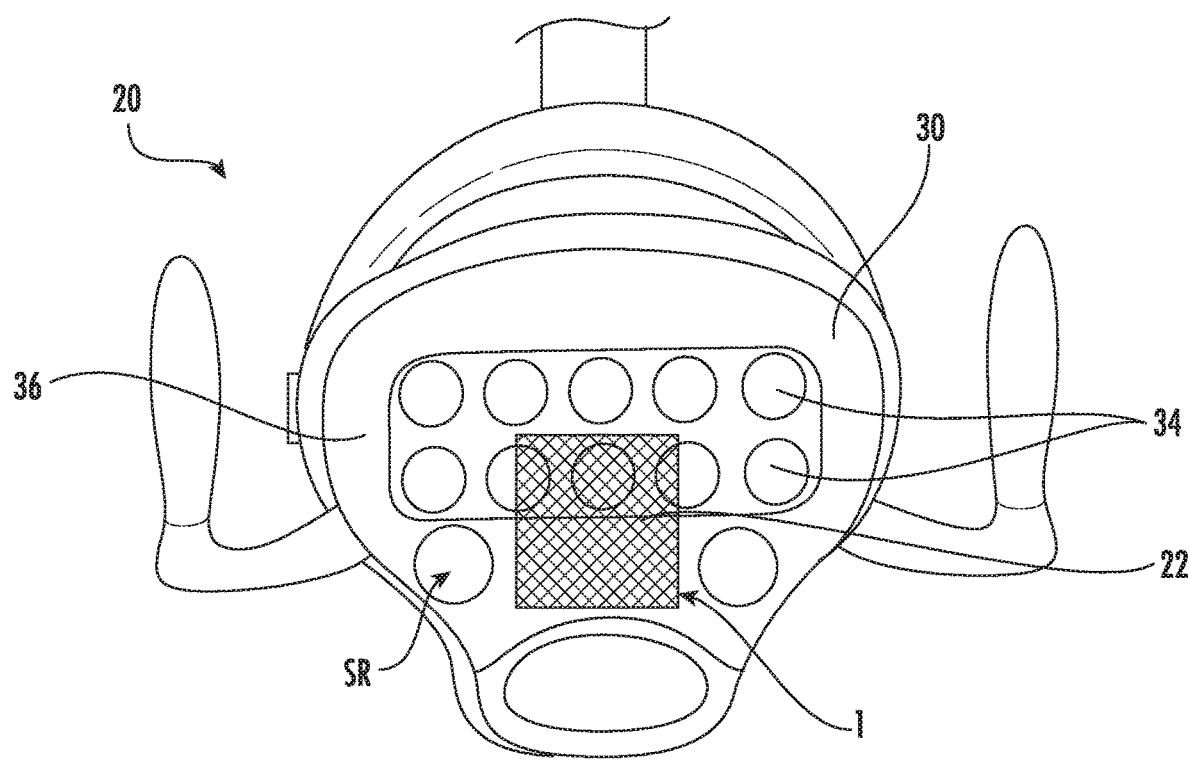

This application claims the benefit of U.S. Provisional Application Ser. No. 63/040,861 filed Jun. 18, 2020 and 63/029,023 filed May 22, 2020, the disclosure of which are incorporated herein by reference in their entirety

BACKGROUND

Embodiments of the disclosure relate to the sanitation or sterilization of aerosols, and more specifically, to the sanitation or sterilization of aerosols generated during a dental procedure.

Processes for cleaning and decontaminating work surfaces and tools or instruments after performing a medical or dental procedure exist and typically includes the use of electrostatic, ultraviolet, or chemical cleaning. However, management of aerosols and preventing the transmission of aerosols contaminated with bacteria, viruses or other microbes during such a procedure, and particularly during procedures where access to a patient's users mouth is required, has posed a challenge for the dental industry. In particular, the use of water cooled high speed hand pieces or ultrasonic scalers cause a patient to produce large quantity of aerosols. These aerosols can potentially infect the operator and/or can settle on surrounding surfaces posing possible health risks.

SUMMARY

According to an embodiment, a sanitation system for use in an application where contaminated aerosols are exhausted by a person includes at least one light source selectively operable to emit a light having a wavelength capable of neutralizing particles and that does not penetrate human skin. The sanitation system additionally includes a mounting system operable to mount said at least one light source. The mounting system is configured to direct the light emitted from the at least one light source toward the person such that the particles are neutralized as the particles are exhausted by the person.

In addition to one or more of the features described above, or as an alternative, in further embodiments

BRIEF DESCRIPTION OF THE DRAWINGS

The following descriptions should not be considered limiting in any way. With reference to the accompanying drawings, like elements are numbered alike:

FIG. 1 is a perspective view of an example of a dental light including a sanitation system according to an embodiment;

FIG. 2 is a perspective view of an example of another dental light including a sanitation system according to another embodiment;

FIGS. 3A and 3B are various configurations of a light concentration assembly relative to a light source of a sanitation system according to an embodiment;

FIG. 4A is a schematic diagram of a lens of a light concentration assembly for use with a sanitation system according to an embodiment;

FIG. 4B is a schematic diagram of a microlens array of a light concentration assembly for use with a sanitation system according to an embodiment; and FIG. 5 is a perspective view of another sanitation system according to an embodiment.

DETAILED DESCRIPTION

A detailed description of one or more embodiments of the disclosed apparatus and method are presented herein by way of exemplification and not limitation with reference to the Figures.

A sanitation system 20 for sanitizing, and in some embodiments sterilizing, all or at least a portion of the aerosols generated by a patient, such as during a medical or dental procedure for example, is illustrated. As used herein, the terms "sanitize" and "sterilize" are intended to indicate neutralizing, killing or otherwise rendering harmless bacteria or airborne viruses or microbes generated by a patient. Further, the sanitation system 20 is operable to perform this sanitation or sterilization in real time, such that the contaminated aerosols are sanitized or sterilized instantaneously as they are exhausted from the patient. It should be understood that the exhausting of contaminated aerosols herein may include aerosols resulting from breathing, coughing, sneezing, as well as aerosols generated as a result of the use of one or more medical or dental instruments.

The sanitation system 20 includes at least one light source 22 capable of emitting a light having a wavelength suitable to perform germicidal irradiation. Existing ultraviolet wavelengths that are commonly used to perform germicidal irradiation have a wavelength of 250-280 nm and cause significant damage to skin and eyes as it penetrates deeply into tissues. Accordingly, these ultraviolet wavelengths are not suitable for use in the presence of humans.

Because the light source 22 of the sanitation system 20 will be operated in the presence of at least one human, the wavelength selected must be safe for humans. In an embodiment, the light source 22 is operable to emit a germicidal ultraviolet light, such as having a wavelength between about 200 and about 230 nanometers, also known as "far-UVC." In an embodiment, the light source 22 is configured to emit light having a wavelength of 222 nm. The shorter wavelength of far-UVC light is not capable of penetrating or damaging living human cells. However, bacteria or viruses are so small that the far-UVC light can easily penetrate the entire virion particle and exert maximum disruption of viral nucleic acid sequences in a very short time. As a result, far-UVC light is able to inactivate viral particles rapidly before they are able travel any significant distance. However, it should be understood that a light having any wavelength capable of neutralizing or irradiating bacteria, viruses or microbes that will not damage human cells is contemplated herein.

Additionally, a light source 22 having any configuration, such as an individual bulb, a light strip having a plurality of bulbs or light emitting diodes, a microplasma lamp, or another type of emitter, is within the scope of the disclosure. In embodiments of the sanitation system 20 including a multiple light sources 22, a configuration of the light sources 22 may be substantially identical, or alternatively, may vary based on a position of the light source.

With reference to FIGS. 1 and 2, various examples of a sanitation system 20 are shown. In each of these embodiments, the sanitation system 20 is mounted to an existing dental light fixture 30. As shown, in an embodiment, the light source 22 is configured to attach to a portion of the dental light fixture 30, such as a handle 32 thereof for example. The light source 22 may include a mounting assembly 24 including an adjustable arm 26 connected to a mounting bracket 28 at a first end and a retention clip 29 at the other. The mounting bracket 28 is configured to connect to the portion of the dental light fixture 30 and the retention clip 29 is configured to receive the one or more light sources 22. In other embodiments, such as shown in FIG. 2, the light source 22 may be integrated directly into a portion of the dental light fixture 30. As shown, the light source 22 is positioned in overlapping arrangement with or directly adjacent one or more light sources 34 of the dental light fixture 30.

By connecting the at least one light source 22 to a portion of the dental light fixture 30, such as the handle 32 or the head 36 thereof, the light source 22 is movable with the dental light fixture 30 for optimal positioning relative to a patient to cleanse contaminated aerosols as they are generated. However, the light source 22 of the sanitation system 20 may also be moved independently of the dental light fixture 30.

Power for the light source 22 could be provided using the existing wiring located in a conduit arm of the dental light fixture 30, or alternatively, could be provided from a separate power source (not shown). Regardless, the light source 22 of the sanitation system 20 may be operated independently of or in combination with the lights 34 of the dental light fixture 30. Although the sanitation system 20 is illustrated and described herein with reference to a dental light fixture 30, it should be understood that the sanitation system may be adapted for use with other tools commonly used during a medical or dental procedure, including tools that are inserted into a patient's mouth.

The intensity or fluence of a light typically varies based on a distance relative to the light source 22. During a dental procedure, the sanitizing light source 22 mounted to the dental light fixture 30 will be positioned at a distance of between 1-5 feet from the patient, and in some embodiments, about 1-4 feet, about 1-3 feet, or about 1-2 feet from the patient. In view of this distance, it is important to design the sanitation system 20 to achieve a necessary fluence of the light output by the light source 22 at the source of the aerosol generation. For example, the necessary fluence of the light at a patient's mouth must be sufficient to neutralize or irradiate bacteria, viruses or microbes expelled therefrom.

Figure 3A:
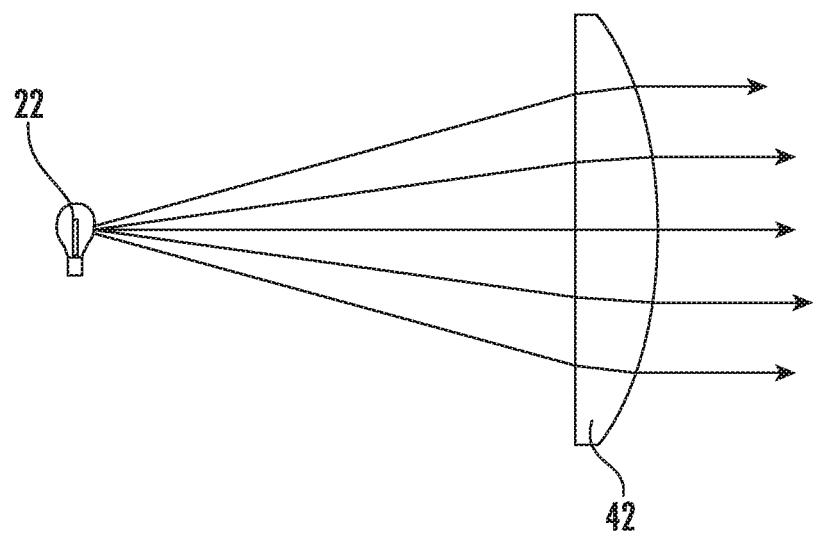
Figure 3B:
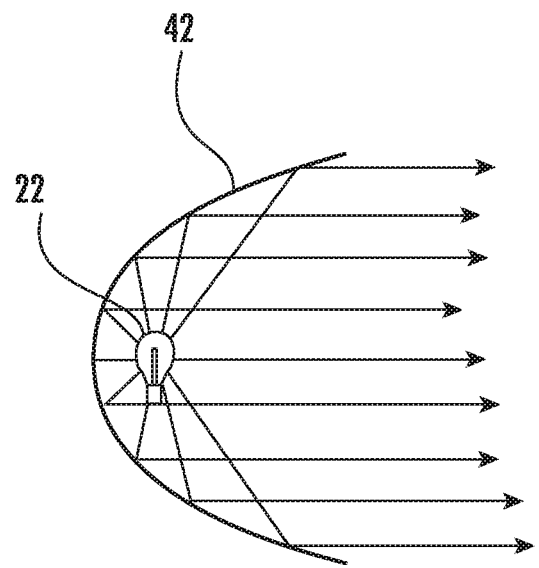
Figure 4A:
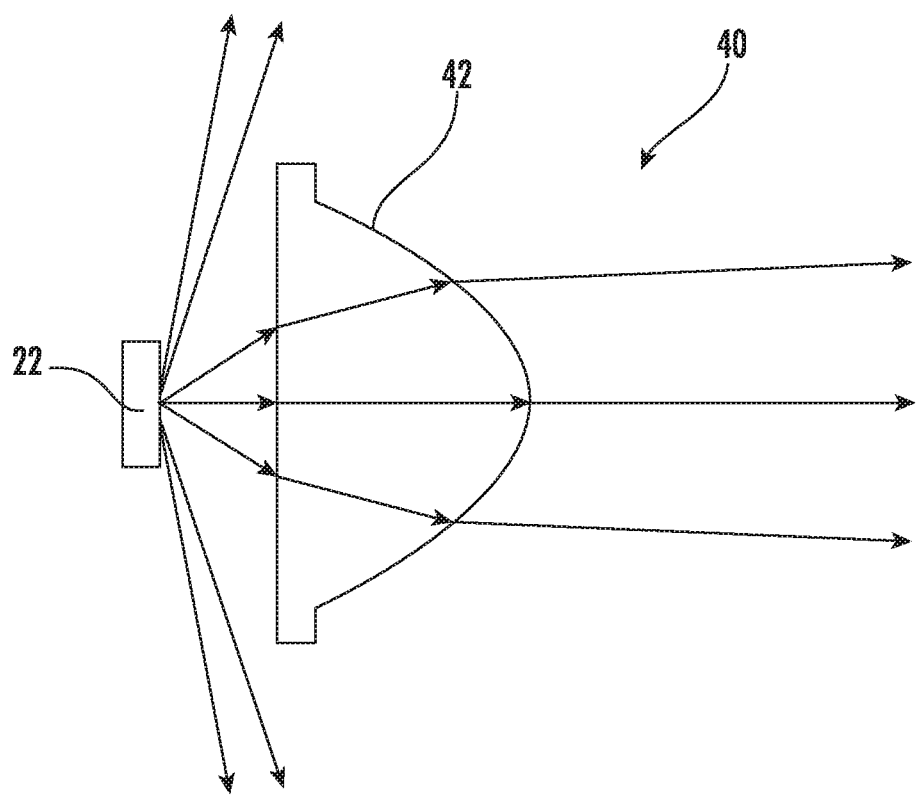
Figure 4B:
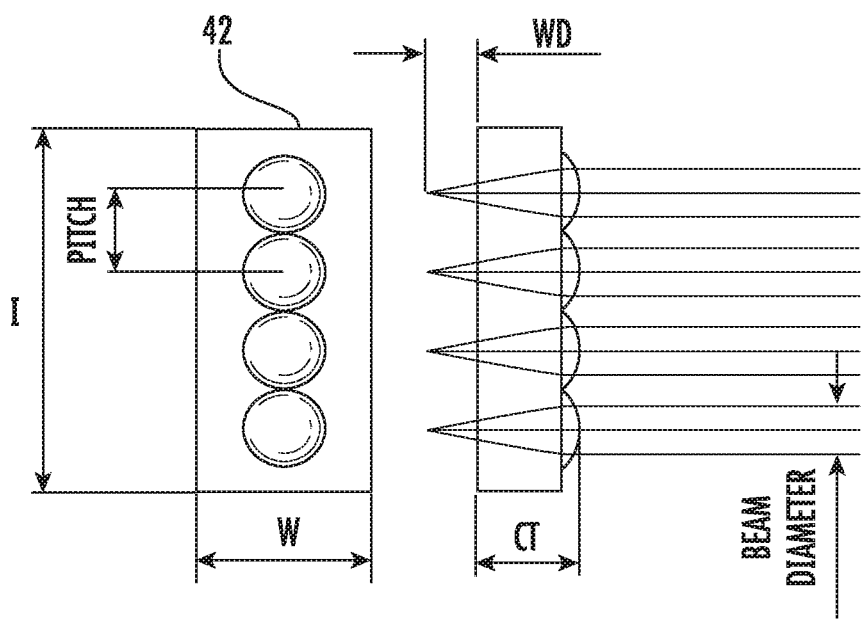

To achieve the necessary fluence at a distance of up to 5 feet, such as 1-3 feet from the light source 22, a light concentration assembly 40 may be positioned adjacent to the light source 22. In an embodiment, light concentration assembly 40 is configured such that a fluence of the light emitted by the light source is at least 75% of the fluence of the light at the light source 22, and in some embodiments is at least 80%, at least 85%, at least 90% or at least 95%. Depending on the components thereof, the light concentration assembly 40 may be arranged at a position between the light source 22 and the source of the aerosol generation (FIG. 3A). Alternatively, or in addition, at least a component 42 of the light concentration assembly 40 may be positioned adjacent a backside of the light source 22, as shown in FIG. 3B, such that the light source 22 is positioned between the component 42 and the source of the aerosol generation. With reference now to FIGS. 3A, 3B, and 4A, in an embodiment, the at least one component 42 of the light concentration assembly 40 includes a lens, parabolic reflector, and/or a mirror made from a suitable material to collimate or concentrate the light output from the light source 22 while preserving the fluence thereof. Examples of suitable lenses include Plano-Convex and Convex-Plano lenses that may or may not have a mirrored surface. Such lenses may be used to minimize geometric dilution corresponding to point-source radiation into three-dimensional space ($1/R^2$), by channeling/concentrating the light from the light source 22 to the source of the aerosol generation. In another embodiment, best shown in FIG. 4B the light concentration assembly includes a plurality or array of microlenses 42 that cooperate to form a collimated output beam having desired characteristics including fluence. In yet another embodiment, the one or more components 42 of the light concentration assembly 40 include at least one planar optical element having one or more layers of phase shifting nanostructures, such as metalenses/collimators, concentrators, beam deflectors with near unity transmission/reflection efficiency.

Although the light concentration assembly 40 is illustrated as being separate from and associated with the light source 22, embodiments where the light concentration assembly 40 is integrated into a portion of the light source 22, such as within the housing of the light source 22 for example, are also within the scope of the disclosure. In such embodiments, the light concentration assembly 40 may be mounted within an interior of the housing of the light source, for example via optical glue. Alternatively, the light concentration assembly 40 may be integrated into the housing itself. For example, the front surface of housing of the light source 22 may be formed from a lens material or may have a lens built therein. Further, in some embodiments, the housing or lens may having integrated conducting grids associated or integrally formed therewith.

Figure 5:
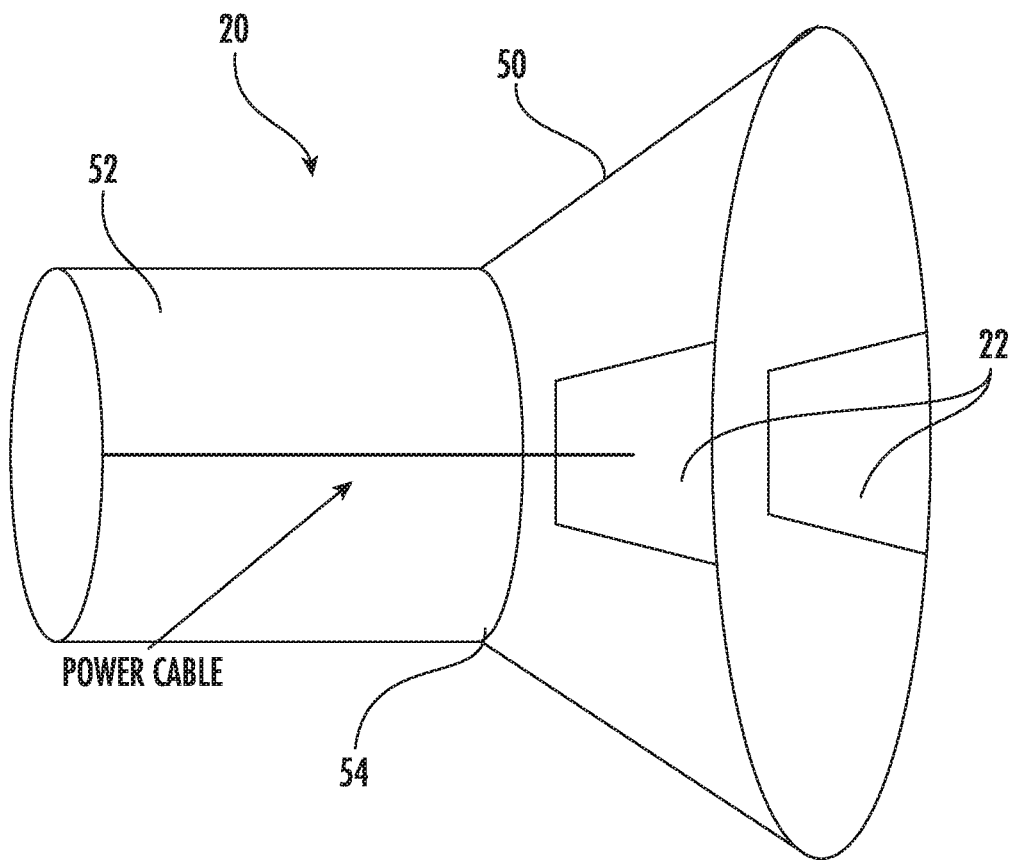

In another embodiment, illustrated in FIG. 5, the sanitation system 20 includes a funnel 50 having a vacuum source 52 connected to a first end 54 thereof. The vacuum source 52 is selectively operable to vector and collect aerosol emitted by the patient. Specifically, the vacuum source 52 and the funnel 50 cooperate to direct the emitted aerosols away from patient and doctor in real time during production of these aerosols. In an embodiment, the one or more light sources 22 of the sanitation system 20 may be positioned to emit light along all or a portion of the flow path of the aerosols defined by the vacuum source 52 and the funnel 50. Although two substantially identical light sources 22 are shown mounted to the funnel 50 approximately 180 degrees apart, any suitable position of the one or more light sources 22 is contemplated herein. Further, in an embodiment, the one or more light sources 22 may be positioned to emit light away from the funnel 50, such as toward a patient's face, to sanitize any aerosols that are not directed into the funnel 50. However, it should be understood that the viruses, bacteria, or other microbes evacuated by the sanitation system may be sanitized or neutralized via any suitable method, and/or at any position remote from the patient. The sanitation system 20 of FIG. 5 is intended to be positioned generally adjacent the source of the aerosol generation, such as within about a foot of a patient's mouth for example. Accordingly, the sanitation system of FIG. 5 need not include a light concentration assembly 40. However, embodiments where a sanitation system 20 including a funnel 50 and vacuum source 52 includes a light concentration assembly 40 are also within the scope of the disclosure.

The purpose of the various sanitation systems illustrated and described herein is to mitigate or eradicate the contamination within the aerosol there by complimenting personal protective equipment for the dental team and further aiding the sanitization of the operatory.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A dental system for use in an application where contaminated particles are exhausted by a person, the dental system comprising:
    a movable dental light fixture having a first light source operable to emit a visible light;
    at least one second light source separate from the first light source, the at least one second light source being selectively operable to emit a light having a wavelength capable of neutralizing contaminated particles, wherein the wavelength does not penetrate human skin, said first visible light source and the at least one second light source are simultaneously operable; and
    a mounting system for mounting said at least one second light source to the movable dental light fixture, the mounting system being connectable to the dental light fixture such that the at least one second light source is positionable at a location offset from the dental light fixture in at least one direction, the mounting system configured to direct the light emitted from the at least one second light source toward the person such that the contaminated particles are neutralized as the particles are exhausted by the person.

2. The system of claim 1, wherein the at least one second light source emits far-UVC light.

3. The system of claim 1, wherein the at least one second light source emits light having a wavelength of about 222 nm.

4. The system of claim 1, wherein the at least one second light source is positioned in overlapping arrangement with or directly adjacent to the first light source of the dental light fixture.

5. The system of claim 4, wherein the mounting system is connected to a handle of the dental light fixture.

6. The system of claim 4, wherein the mounting system is connected to a head of the dental light fixture.

7. The system of claim 4, wherein the mounting system further comprises:
    a mounting bracket for mounting the at least one second light source;
    a retention clip; and
    an adjustable arm connected to the mounting bracket at a first end and the retention clip at a second end.

8. The system of claim 4, wherein the at least one second light source is movable with the dental light fixture.

9. The system of claim 4, wherein the at least one light source is movable independently of the dental light fixture.

10. The system of claim 9, further comprising a light concentration assembly positioned adjacent the at least one light source.

11. The system of claim 10, wherein the light concentration assembly includes at least one of a lens, mirror, or reflector.

12. The system of claim 10, wherein a fluence of the light emitted by the light source is at least 80% of the fluence of the light at the light source.

* * * * *